US010530083B2

(12) United States Patent
Dumont

(10) Patent No.: US 10,530,083 B2
(45) Date of Patent: Jan. 7, 2020

(54) PRINTED CIRCUIT BOARD BIOSENSING GARMENT CONNECTOR

(71) Applicant: Honeywell Safety Products USA, Inc., Fort Mill, SC (US)

(72) Inventor: Thierry Dumont, Montréal (CA)

(73) Assignee: HONEYWELL SAFETY PRODUCTS USA, INC., Fort Mill, SC (US)

( * ) Notice: Subject to any disclaimer, the term of this patent is extended or adjusted under 35 U.S.C. 154(b) by 80 days.

(21) Appl. No.: 15/812,455

(22) Filed: Nov. 14, 2017

(65) Prior Publication Data
US 2018/0138616 A1 May 17, 2018

Related U.S. Application Data

(60) Provisional application No. 62/422,896, filed on Nov. 16, 2016.

(51) Int. Cl.
*H01R 33/00* (2006.01)
*H01R 12/77* (2011.01)
(Continued)

(52) U.S. Cl.
CPC ......... *H01R 12/777* (2013.01); *A61B 5/0015* (2013.01); *A61B 5/6804* (2013.01);
(Continued)

(58) Field of Classification Search
CPC .. H01R 12/777; H01R 13/03; H01R 13/6675; H05K 1/028; H05K 1/111; A61B 5/0015; A61B 5/6804
(Continued)

(56) References Cited

U.S. PATENT DOCUMENTS 3,700,443 A * 10/1972 Reimann ................ H05K 1/111
174/261
5,380,271 A 1/1995 Gyory
(Continued)

FOREIGN PATENT DOCUMENTS

CA 2 689 267 A1 12/2008
WO WO 2016/142873 A1 9/2016
(Continued)

OTHER PUBLICATIONS

International Search Report and Written Opinion dated Jan. 18, 2018 for International Application No. PCT/CA2017/051365, 9 pages.

*Primary Examiner* — Hae Moon Hyeon
(74) *Attorney, Agent, or Firm* — Alston & Bird LLP

(57) ABSTRACT

In some embodiments, an apparatus comprises a biosensing garment and an electronics assembly. The biosensing garment includes a sensor, a conductive pathway, and a connection region including one or more connectors that are disposed on a PCB. The connection region is electrically coupled to the conductive pathway and the sensor. The connection region is further configured to be electronically coupled to the electronics assembly via at least one conductive contact. In some embodiments, the electronics assembly includes at least one conductive contact that is configured to be electronically coupled to at least one portion of the PCB.

20 Claims, 27 Drawing Sheets
(8 of 27 Drawing Sheet(s) Filed in Color)

(51) Int. Cl.
*A61B 5/00* (2006.01)
*H01R 13/03* (2006.01)
*H01R 13/66* (2006.01)
*H05K 1/02* (2006.01)
*H05K 1/11* (2006.01)

(52) U.S. Cl.
CPC ......... *H01R 13/03* (2013.01); *H01R 13/6675* (2013.01); *H05K 1/028* (2013.01); *H05K 1/111* (2013.01); *A61B 5/6831* (2013.01); *A61B 2560/0214* (2013.01); *H01R 2201/20* (2013.01); *H05K 2201/0183* (2013.01)

(58) Field of Classification Search
USPC .......................................................... 439/37
See application file for complete search history.

(56) References Cited

U.S. PATENT DOCUMENTS

| | | | | |
|---|---|---|---|---|
| 6,729,025 | B2* | 5/2004 | Farrell | B32B 3/08 |
| | | | | 29/825 |
| 7,025,596 | B2* | 4/2006 | Zollo | H01R 4/64 |
| | | | | 428/102 |
| 7,484,967 | B2* | 2/2009 | Ichino | H01R 12/62 |
| | | | | 439/329 |
| 2010/0075511 | A1* | 3/2010 | Kim | H01R 11/12 |
| | | | | 439/37 |
| 2011/0119812 | A1* | 5/2011 | Genz | F21V 23/04 |
| | | | | 2/244 |
| 2012/0247824 | A1* | 10/2012 | Ohsawa | G11B 5/486 |
| | | | | 174/264 |
| 2013/0160183 | A1 | 6/2013 | Reho et al. | |
| 2014/0135593 | A1 | 5/2014 | Jayalath et al. | |
| 2015/0380843 | A1* | 12/2015 | Dubal | H01R 13/20 |
| | | | | 439/37 |
| 2016/0038083 | A1* | 2/2016 | Ding | A61B 5/6804 |
| | | | | 600/388 |
| 2017/0035354 | A1 | 2/2017 | Jayalath et al. | |
| 2017/0094800 | A1 | 3/2017 | Keranen et al. | |
| 2017/0237430 | A1* | 8/2017 | Stone | H05K 1/162 |
| | | | | 200/600 |

FOREIGN PATENT DOCUMENTS

| | | |
|---|---|---|
| WO | WO 2017/075703 A1 | 5/2017 |
| WO | WO 2017/146616 A1 | 8/2017 |

* cited by examiner

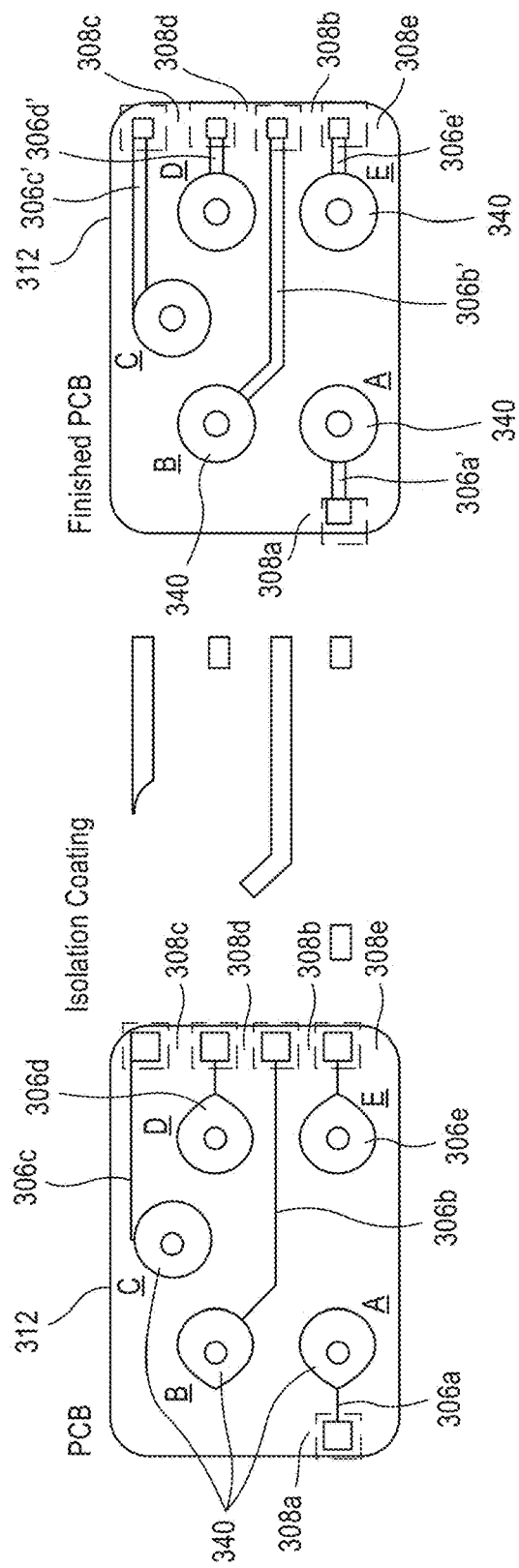

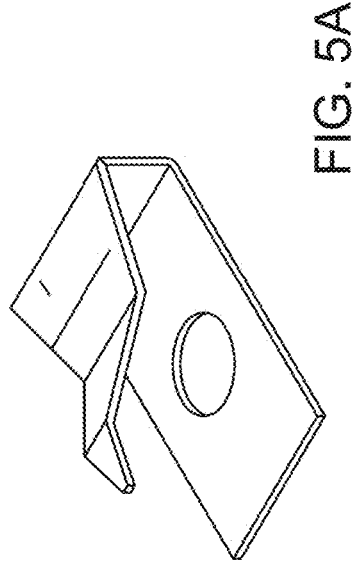
FIG. 5A
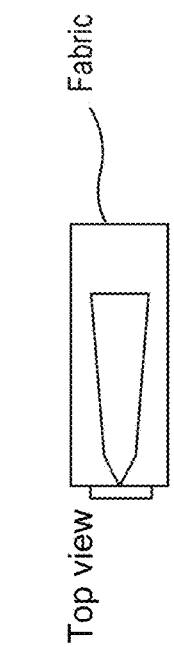
Hook A
FIG. 5B Top view
FIG. 5C Side view

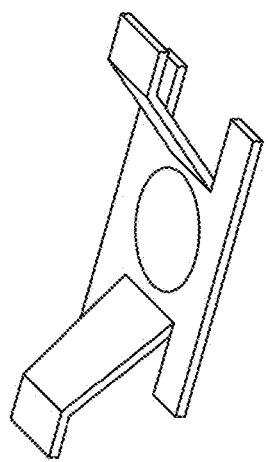
FIG. 6A
Hook B (Cleat)
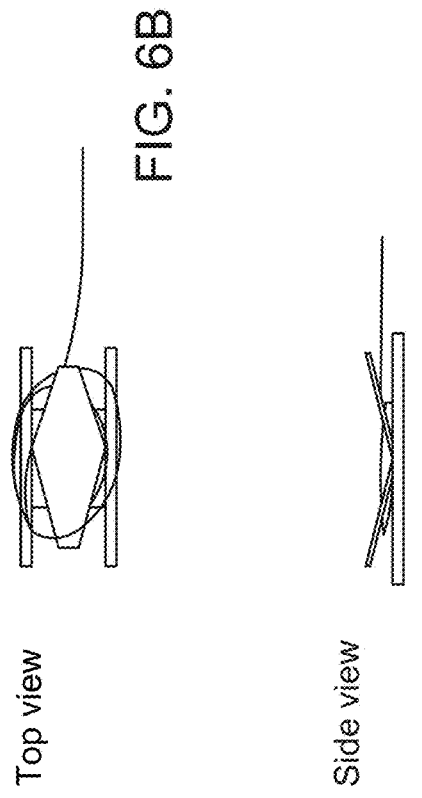
FIG. 6B
Top view
FIG. 6C
Side view

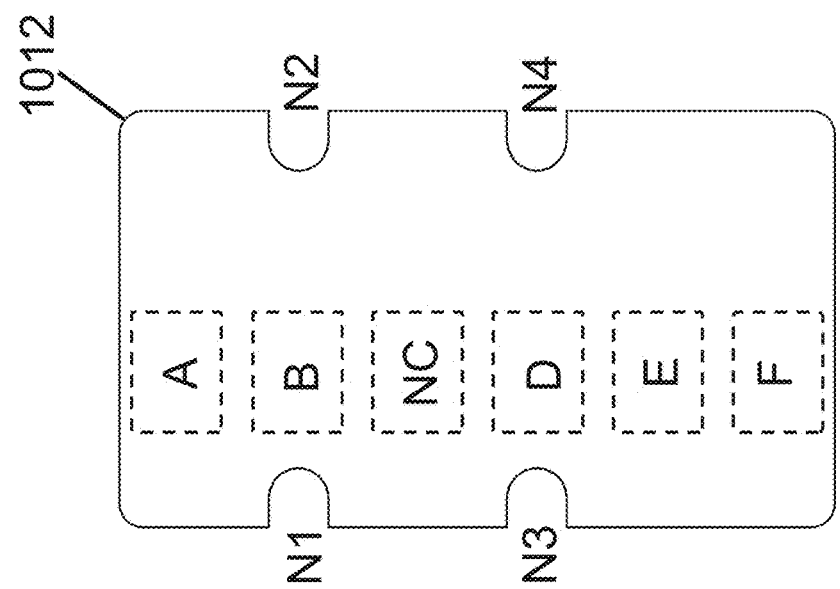
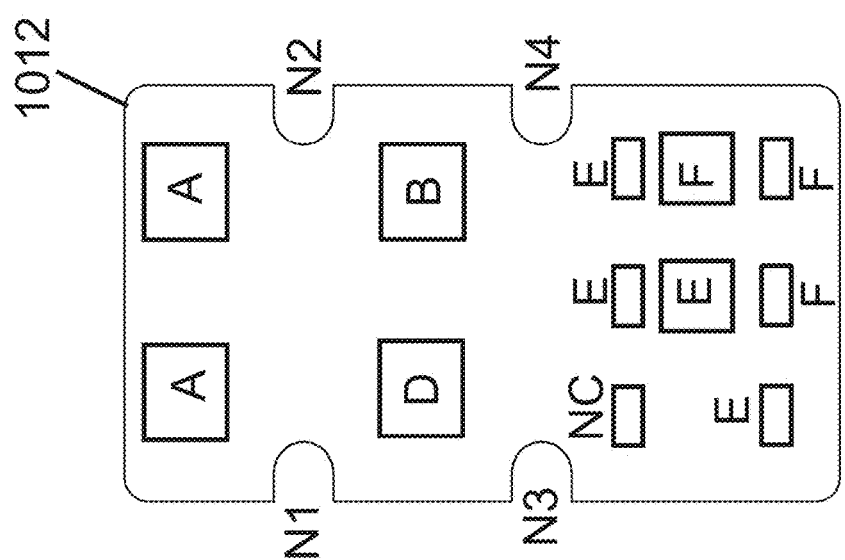
FIG. 12A
FIG. 12B

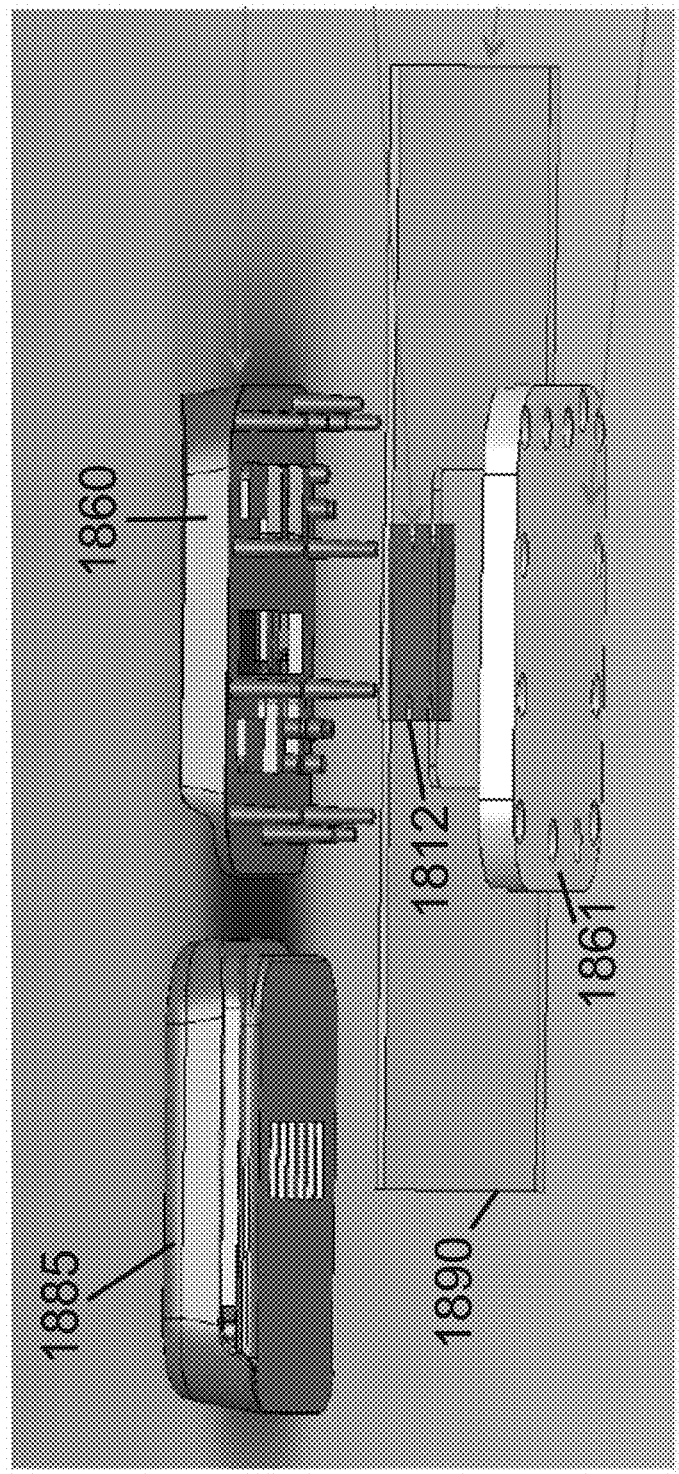

PRINTED CIRCUIT BOARD BIOSENSING GARMENT CONNECTOR

CROSS-REFERENCE TO RELATED APPLICATIONS

This application claims priority to and the benefit of U.S. Provisional Patent Application Ser. No. 62/422,896, filed Nov. 16, 2016 and titled "Printed Circuit Board Biosensing Garment Connector," the disclosure of which is hereby incorporated by reference in its entirety.

BACKGROUND

The adoption of wearable consumer electronics, or "smart clothing," is currently on the rise. Biosensing garments, a subset of wearable electronics, are designed to interface with a wearer of the garment, and to determine information about the wearer's physiology such as cardiac signal (including heart rate), respiration, activity level, body positioning, etc. Such properties can be measured via a sensor assembly in close proximity to the wearer's body, portions of which are in direct contact with the wearer's skin and that receive signals from the wearer's body and activity. Through these sensor assemblies, signals are transmitted to one or more electronic sensors and/or microprocessors for transduction, analysis, display, etc. A drawback of many biosensing garments on the market today, however, is that they are not able to capture signals of sufficiently high resolution, nor are they reliable or durable enough to maintain acceptable performance over time (e.g., signal quality). As such, there is a general need for biosensing garments with improved reliability and durability. A core component of such a system is the connector, wherein the textile component of the sensor assembly interfaces with the electronic sensors and/or microprocessors.

SUMMARY

In some embodiments, an apparatus comprises a biosensing garment and an electronics assembly. The biosensing garment includes a sensor, a conductive pathway, and a connection region including one or more connectors that are disposed on a printed circuit board ("PCB"). The connection region is electrically coupled to the conductive pathway and the sensor. The connection region is further configured to be electronically coupled to the electronics assembly via at least one conductive contact. In some embodiments, the electronics assembly includes at least one conductive contact that is configured to be electronically coupled to at least one portion of the PCB.

BRIEF DESCRIPTION OF THE DRAWINGS

The patent application file contains at least one drawing executed in color. Copies of this patent application with color drawings will be provided by the Office upon request and payment of the necessary fee.

FIGS. 3A-3C illustrate an assembly process of a biosensing garment connector with a PCB interface in accordance with some embodiments. FIG. 3A illustrates a connection region with a PCB interface. FIG. 3B illustrates isolation coating to protect components on the PCB in accordance with some embodiments. FIG. 3C is an illustration of the connector region with finished PCB in accordance with some embodiments.

FIG. 5A illustrates perspective view of a hook attachment in accordance with some embodiments. FIGS. 5B and 5C illustrate top and side views, respectively, of a hook attachment in accordance with some embodiments.

FIG. 6A illustrates a perspective view of a cleat attachment in accordance with some embodiments. FIGS. 6B and 6C illustrate top and side views, respectively, of a cleat attachment in accordance with some embodiments.

FIGS. 12A and 12B are further illustrations of the top and bottom layers, respectively, of the PCB of FIGS. 10 and 11.

FIGS. 18E and 18F illustrate perspective, exploded views of a multilayer assembly for a biosensing garment, in accordance with some embodiments.

DETAILED DESCRIPTION

Figure 1:
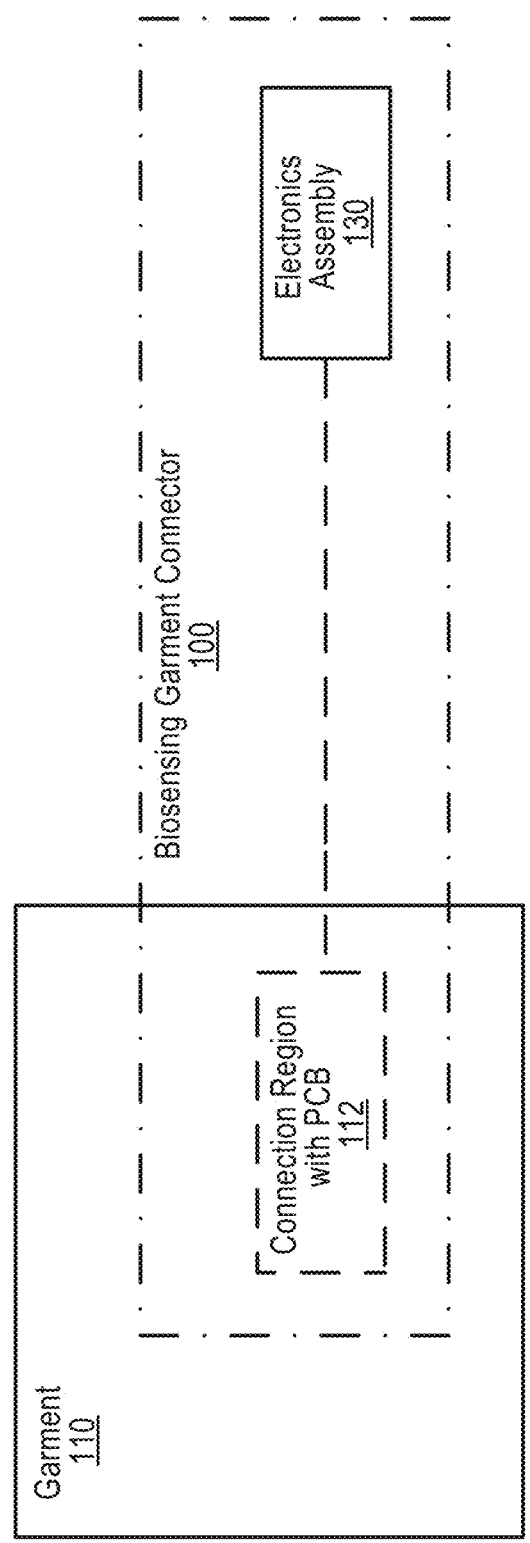
FIG. 1 is a schematic block diagram of a biosensing garment connector, according to an embodiment.

Wearable electronics such as biosensing garments (and the electronic textiles from which they are made) are subjected to different mechanical stresses than traditional electronic systems. For example, biosensing garments may be stretched during enrobing, disrobing, handling, wear (e.g., during physical activity of the wearer), and washing. This stretching can result in deformation, and even detachment, of conductors, sensor elements, connectors, and other components that are embedded within and/or secured to a surface of the biosensing garment. As a result, wearable electronics can suffer from poor signal quality from the onset, as well as compromised performance after only a limited period of use. Also, biosensing garments that include rigid, surface-mounted electronic components can be difficult to manufacture in a scalable way, and are prone to mechanical and/or electrical failure at the interface between the soft, deformable textile component and the electronic components. As a result, many electronic textile prototypes are never brought to market. In some embodiments disclosed herein, biosensing garment connectors are configured to integrate electronic components with a deformable textile component in a manner that improves the electrical and/or mechanical integrity of the assembly.

According to embodiments of the present disclosure, improved biosensing garment connectors with a Printed Circuit Board (PCB) interface are described that integrate textile/garment manufacturing techniques with industrial electronics designs and manufacturing techniques, resulting in improved biosensing garment durability and reliability, as well as improved manufacturing scalability.

Embodiments described herein relate generally to connectors for biosensing applications, such as biosensing garments. In some embodiments, a biosensing garment connector includes a connection region with a PCB and an electronics assembly. The PCB has a plurality of connectors that are configured to electrically connect to conductive members of a garment (e.g., conductive bands or elongate members) via at least one contact pad included on the PCB. In some embodiments, the connectors are electrically connected to the conductive members via an attachment that is coupled to the contact pad. The connectors can be attached to the contact pad or integrally formed with the contact pad. In some embodiments, the attachment can be a hook attachment that is configured to allow conductive members such as conductive bands to be attached to the plurality of connectors. In some embodiments, the attachment can be a cleat attachment onto which conductive members (e.g., elongate wires or filaments) can be looped and/or otherwise wound around. In some embodiments, the PCB can be coupled to a portion of the garment and can comprise a plurality of layers of heat adhesive TPU films and/or flexible yet non-stretchable PET film, such that desired levels of support reinforcement and insulation are achieved. The electronics assembly is configured to electronically connect to the PCB. In some embodiments, the electronics assembly includes at least one conductive contact that is configured to electronically connect to at least a portion of the PCB. In some embodiments, the electronics assembly can include a housing with one or more insulation layers and can be mechanically coupled to the garment via a snap-fit or magnetic attachment.

In some embodiments, an apparatus comprises a biosensing garment and an electronics assembly. The biosensing garment includes a sensor, a conductive pathway, and a connection region including one or more connectors that are disposed on a PCB. The connection region is electrically coupled to the conductive pathway and the sensor. The connection region is further configured to be electronically coupled to the electronics assembly via at least one conductive contact. In some embodiments, the electronics assembly includes at least one conductive contact that is configured to be electronically coupled to at least one portion of the PCB.

In some embodiments, an electronic textile and connector assembly for securely connecting an electronic device to a functional fabric substrate are described. The fabric substrate has one or more conductive pathways that connect one or more integrated sensors to a connection region on the electronic textile. The connection region includes a plurality of connectors that are disposed on a PCB. Sensor types can include electrocardiogram (ECG), breathing (e.g., respiratory inductance plethysmography), movement, temperature, and orientation. Sensors can include textile-based sensors and/or electronic devices. A rigid (yet flexible) electronic device (or "module" or "electronics assembly") is secured to the connection region. Methods for manufacturing such an electronic textile and connector assembly are also described.

Turning now to FIG. 1, a biosensing garment connector 100 includes at least a portion of a garment 110, a connection region 112, and an electronics assembly 130. The connection region 112 is configured to be included in or disposed in the garment 110. Additionally, the connection region 112 can be electronically and mechanically coupled to the electronics assembly 130. In some embodiments, the electronics assembly 130 can be mechanically attached or coupled to the garment 110.

The garment 110 can be any biosensing garment or portion thereof, such as a shirt (e.g., a biometric shirt), shorts, pants, brassiere, headband, arm band, leg band, wrist band, etc. The garment 110 can include one or more conductive members (e.g., conductive bands or elongate members) that electrically attach to, and connect one or more integrated sensors to, the connection region 112 on the electronic textile. Sensor types can include electrocardiogram (ECG), breathing (e.g., respiratory inductance plethysmography), movement, temperature and orientation. Sensors can include textile-based sensors and/or electronic devices, and can be attached to one or more conductive pathways/bands. Conductive bands can be integrated into the garment 110, for example, via knitting with conductive yarns, lamination of a conductive textile, and/or etching of a conductive textile. In some embodiments, the conductive bands are insulated up until they reach the connection region 112. In some embodiments, the conductive members such as conductive pathways and elongate members can be as described in PCT Application No. PCT/CA2016/051274 titled "BIOSENSING GARMENT" filed Nov. 2, 2016, the entire disclosure of which is incorporated herein by reference in its entirety and attached hereto as Exhibit A.

The connection region 112 is mechanically and electrically attached or coupled to a portion of the garment 110. The connection region 112 includes a plurality of connectors disposed on the PCB. The connectors can include and/or be formed from one or more metals, such as copper, aluminum, silver, or any other suitable metal. In some embodiments, the connectors are mounted on the PCB via Surface Mount Technology (SMT). In some embodiments, the connection region 112 includes a plurality of conductive contact pads. The contact pads can include a metal, for example that has been screen-printed, inkjet printed, spray deposited, and/or vapor deposited onto a PCB. In some embodiments, the contact pads can include one or more of a rivet, snap, or any other type of electrically conductive hardware.

In some embodiments, the connection region 112 is included in or disposed in the portion of the garment 110 via one or more of the following connection methods: laminating, bonding, conductive elastomer, sewing, snap flexure, snap-fit (e.g., cantilever, torsion, annular), press-fit, magnetic, screw attach, threaded, riveted, pin-and-socket, adhesive, Velcro®, welding, solvent bonding, clip attach, and/or any other connection method. In some embodiments, one or more edges of the connection region 112 can include a composite material (e.g., comprising rubber, silicone, or other flexible material) for increased flexibility, and/or the connection region 112 can have a hinged design. In some embodiments, the connection region 112 can comprise an insulating material such as plastic (e.g., injection-molded plastic), silicone, or rubber. In some embodiments, connection region 112 can include one or more electrical contacts, such as conductive contact pads, prongs, pogo pins, and/or the like. The electrical contacts can comprise and/or be formed from one or more metals, such as copper, aluminum, gold silver, carbon (e.g., carbon nanotubes), or any other suitable metal. Alternatively or in addition, the electrical contacts can comprise and/or be formed from one or more nonmetal conductors, such as a conductive polymer. In some embodiments, connection region 112 can be coupled to an electronics assembly 130 via contact pads with a snap-fit attachment.

In some embodiments, the connection region 112 can be electronically and mechanically coupled to the electronics assembly 130 via at least one contact pad. The electronics assembly 130 can contain one or more of: a battery (e.g., a rechargeable battery), an antenna, a receiver, a transmitter, a transceiver, one or more sensors, and a microprocessor. The electronics assembly 130 can include an electronics assembly body (or "housing") that is formed from an insulating material such as plastic (e.g., injection-molded plastic), silicone, or rubber, a combination of various materials of varying mechanical properties, or any other suitable material. The electronics assembly 130 can be rigid (e.g., to protect electronics contained therewithin from mechanical damage), or can be flexible, for example in embodiments where the electronics contained therewithin are sufficiently protected by virtue of their own packaging, or a combination of various materials of varying mechanical properties. The electronics assembly 130 can have a shape that is comfortable to a wearer (e.g., rounded corners, smooth surface(s), etc.) and/or that is ergonomic or deformable, such as comprising several contiguous articulated segments. In some embodiments the electronics assembly body can be mechanically coupled to the garment via a snap-fit or magnetic attachment.

Figure 2:
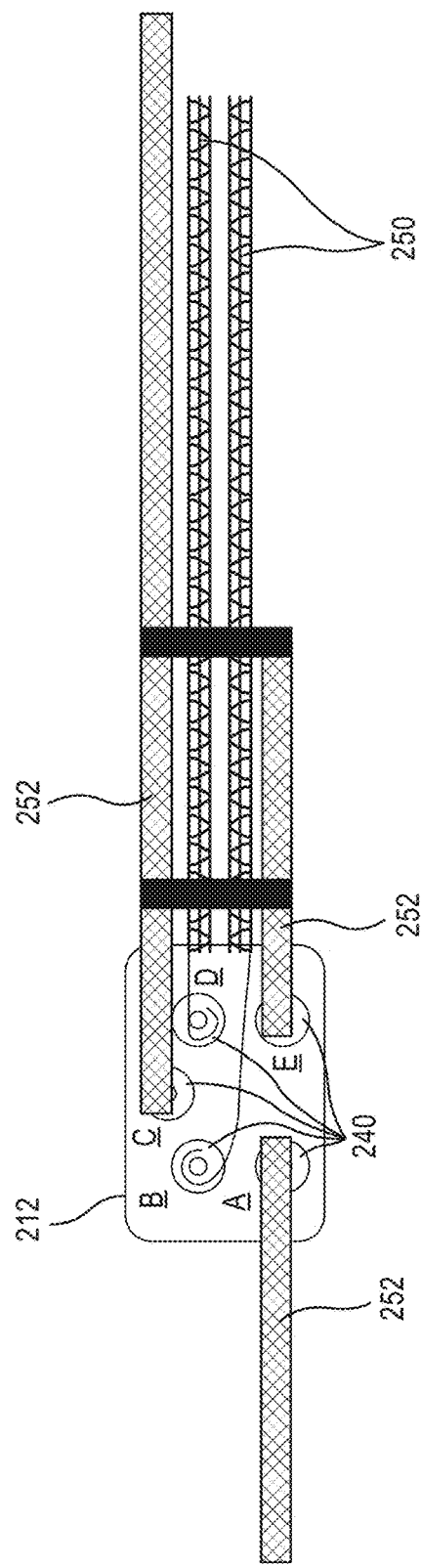
FIG. 2 is an illustration of conductive pathways, plurality of connectors, connection region without PCB, and elongate members in accordance with some embodiments.

FIG. 2 is an illustration of conductive pathways and elongate members coupled to a plurality of connectors in a connection region in accordance with some embodiments. In some embodiments, a plurality of connectors such as A, B, C, D and E, collectively 240 can be disposed on a connector base. The connector base can comprise a plurality of layers of heat adhesive TPU films and/or a flexible yet non-stretchable PET film, such that desired levels of support, reinforcement and insulation are achieved. The connectors 240 and the connector base form a connection region 212. In such embodiments, the conductive members such as conductive pathways/bands 252 are connected to the connectors 240 at a portion of the garment via stainless steel snaps (e.g., comprising an S-spring socket and a hidden cap, or "snap cap"). The caps can comprise stainless steel, brass, or any other suitable (i.e., biocompatible) material. In between the socket and the cap of each of the 5 snaps, a section (e.g., a round section) of conductive tape can be inserted/disposed to ensure a proper electrical connection between the hidden cap and the conductive pathway/band (e.g., conductive bands, elastic, trace, wire, etc.) that is attached to it. For example, the conductive tape ring can be inserted in between the metal plate and the hidden cap and the conductive pathway prior to pressing the snap. In FIG. 2, the connectors A, C and E are connected to the conductive bands 252 that can be attached to textile based sensors (e.g., ECG sensors).

Connectors B and D are connected to conductive members such as elongate members 250 (e.g., a RIP/breathing sensor) that extends or is looped around the garment. The elongate members 250 can be a stretchable tape that is knitted with a conductive wire or filament that is disposed in sinusoidal shape. The elongate members 250 can be partially attached to a band/elastic, e.g., with TPU pieces/strips that are used to bond the elongate member to the band/elastic. The TPU pieces/strips can also be further stitched to secure the connection to the band/elastic. The same snaps as described above (stainless steel S-spring sockets and hidden caps) can be used to connect elongate members 250 to connectors B and D. In between the socket and the cap of the snaps B and D, a layer (e.g., a ring) of thin PET film can be inserted/disposed, for example to secure elongate members 250 tightly against bottom plate when connected (e.g., during assembly). Alternatively or in addition, to further secure the electrical connection, a ring of conductive adhesive tape can be inserted between the socket and cap of the snaps (e.g., such that the conductive member is sandwiched between the snap cap and the ring conductive adhesive tape, and ring of conductive adhesive tape is attached to the lower/inside surface of the PET ring). In such configurations, the components are disposed in the following order: snap cap, conductive member, conductive adhesive tape, PET film ring.

In embodiments as shown in FIG. 2 and described herein, the plurality of connectors 240 may need to be placed in pre-defined configurations to ensure connectivity between the connectors 240 and the conductive members (e.g., conductive pathways/bands 252 and elongate members 250). Further, the pre-defined configurations may impose size restrictions during manufacturing of such biosensing garment connectors. In addition, such biosensing garment connectors may be prone to mechanical and/or electrical failure due direct mechanical coupling between rigid connectors 240 and deformable conductive members.

In some embodiments described herein, a connection region can include a flexible PCB interface. In such embodiments, the connectors can be disposed on the flexible PCB for example, using SMT, and the PCB interface allows for greater design flexibility since the connectors can be disposed in multiple configurations on the PCB and can still guarantee electrical connectivity.

FIGS. 3A-C illustrate an assembly process of a biosensing garment connector with a PCB interface in accordance with some embodiments. FIG. 3A illustrates a connection region 312 with a PCB interface. Connectors 340, traces 306a-306e, and contact pads 308a-308e are disposed and/or integrated into the PCB.

The PCB can be disposed in a portion of a garment via one or more of the following connection methods: laminating, bonding, conductive elastomer, sewing, snap flexure, snap-fit (e.g., cantilever, torsion, annular), press-fit, magnetic, screw attach, threaded, riveted, pin-and-socket, adhesive, Velcro®, welding, solvent bonding, clip attach, and/or any other connection method. In some embodiments, one or more edges of connection region 312 can include a composite material (e.g., comprising rubber, silicone, or other flexible material) for increased flexibility, and/or the connection region 312 can have a hinged design.

In some embodiments, a plurality of connectors for example, A, B, C, D, and E (collectively 340) are disposed on the PCB via surface-mount technology ("SMT"). Connectors 340 can comprise and/or be formed from one or more metals, such as copper, aluminum, gold, silver, carbon (e.g., carbon nanotubes), or any other suitable metal. In some embodiments, connectors 340 can include stainless steel snaps (e.g., comprising an S-spring socket and a hidden cap, or "snap cap") or other snap-fit attachments to provide electronic and mechanical coupling with external devices such as an electronics assembly (e.g., electronics assembly 130 in FIG. 1).

In some embodiments, the PCB includes one or more contact pads, for example 308a, 308b, 308c, 308d, and 308e (collectively 308), that provide for mechanical and electrical coupling between the connectors 340 and conductive members (e.g., elongate member 250 and conductive pathways/bands 252 in FIG. 2). In some embodiments, the contact pads 308 are coupled to attachments that connect the conductive members with the contact pads 308. In some embodiments, conductive members such as conductive pathways/bands are connected to the contact pads 308 via a hook attachment. In some embodiments, conductive members such as elongate members are connected to the contact pads 308 via a cleat attachment. Traces such as 306a, 306b, 306c, 306d and 306e (collectively 306) connect the contact pads 308 with the connectors 340.

For instance, say connectors A, C, and E are to be connected to conductive members such as conductive pathways/bands (e.g., conductive band 252 in FIG. 2) and connectors B and D are to be connected to conductive members such as elongate members (e.g., elongate member 250 in FIG. 2). The trace 306a connects the connector A with the contact pad 308a. In a similar manner, traces 306c and 306e connect the connectors C and E with the contact pads 308c and 308e respectively. In some embodiments, hook attachments can be coupled to contact pads 308a, 308c, and 308e. One or more conductive pathways/bands are electrically coupled to the contact pads 308a, 308c, and 308e via the hook attachments. Thus, electrical connection is established between the connectors A, C, and E and the conductive pathways/bands. Traces 306b and 306e connect the connectors B and D with the contact pads 306b and 306d respectively. In some embodiments, cleat attachments can be coupled to contact pads 308b and 308e. Elongate members are electrically coupled to the contact pads 308b and 308d via the cleat attachments. In some embodiments, elongate members can be wound/looped around the cleat attachments to provide for flexibility and slack. Thus, electrical connection is established between the connectors B and D and elongate members. In this manner, electrical connection can be established between the connectors 340 and conductive members despite the orientation or configuration of the connectors 340 on the PCB thereby facilitating flexibility in form factor/design.

FIG. 3B illustrates isolation coating to protect components on the PCB in accordance with some embodiments. The isolation coating can be used to isolate the conductive traces on the PCB. In some embodiments, coating material such as a thin polymeric film is used to protect the components on the PCB such as traces 306 from varying conditions and to prevent the PCB from corroding. In some embodiments, the isolation coating reduces short circuit risk on the electronic assemblies included in the PCB. The coating material can be applied by methods such as brushing, spraying, dipping and/or the like. FIG. 3B illustrates coating to protect traces 306a, 306b, 306c, 306d, and 306e.

FIG. 3C is an illustration of the connector region 312 with finished PCB in accordance with some embodiments. Isolation coating is applied on the traces 306 and the finished PCB with traces (including the isolation coating) 306' (for example, 306a'. 306b', 306c', 306d', and 306e') are illustrated. In some embodiments, the one or more of the traces 306 can have more than one contact point with the connectors 340. In other words, the trace 306 can split into a "Y" shape and contact the connector 340 at two locations (e.g., at opposite sides of the connector 340). The multiple contact points can improve durability because of the redundant conductive pathways.

Figure 4A:
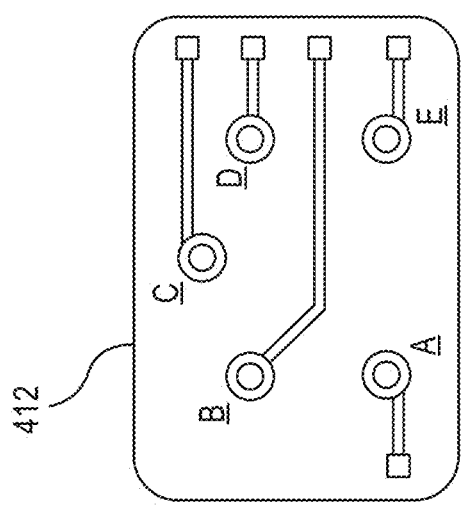
FIGS. 4A-4C illustrate connector regions with connectors, disposed in different configurations, in accordance with some embodiments.
Figure 4B:
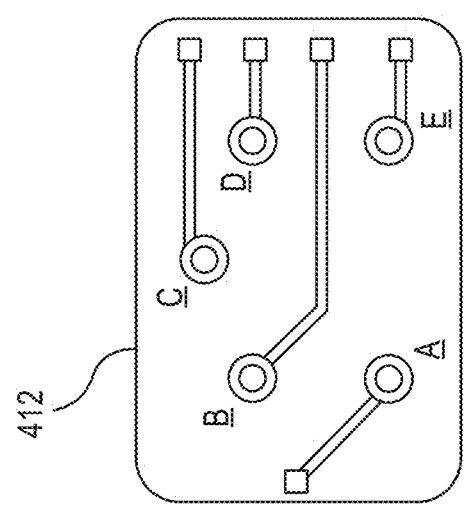
Figure 4C:
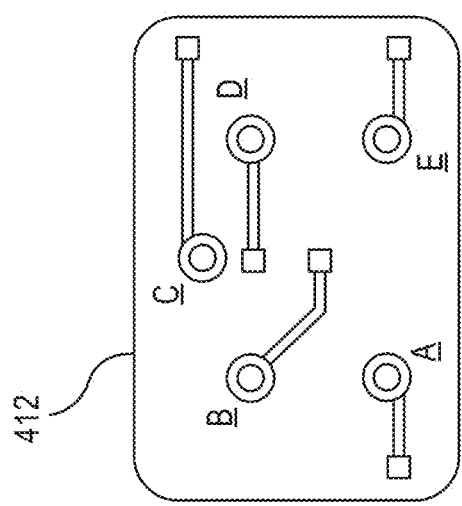

FIGS. 4A-C illustrate connector region 412 with connectors 440 disposed in different configurations in accordance with some embodiments allowing for flexibility in form factor and/or design. In addition, the number of contacts and traces can easily be increased or decreased.

FIG. 5A illustrates perspective view of a hook attachment in accordance with some embodiments. In some embodiments, the hook attachment can be coupled to contact pads on the connection region. The hook attachment can electrically couple conductive members such as conductive pathways/bands to the PCB. In some embodiments, the conductive pathways are conductive elastic bands for example, including a plurality of elastic filaments disposed substantially parallel to one another and mechanically coupled to one another by one or more conductive and/or non-conductive filaments that are knotted or woven about the elastic filaments. The conductive bands can be integrated into the garment, for example, via knitting with conductive yarns, lamination of a conductive textile, and/or etching of a conductive textile. The hook attachment can be manufactured from one or more metals, such as copper, aluminum, gold, silver, carbon (e.g., carbon nanotubes), or any other suitable metal. In some embodiments, one or more of layers of heat adhesive TPU films can be disposed over the hook such that desired levels of support, reinforcement and insulation are achieved. FIGS. 5B and 5C illustrate top and side view of the hook attachment respectively in accordance with some embodiments.

FIG. 6A illustrates perspective view of a cleat attachment in accordance with some embodiments. In some embodiments, the cleat attachment can be coupled to contact pads on the connection region. The cleat attachment can electrically couple conductive members such as elongate members to the PCB. In some embodiments, the elongate members can include a RIP sensor, for example including a conductive member that is mechanically coupled (e.g., via knitting, weaving, threading, twisting, folding, wrapping, braiding, adhesion, or any other method of attachment) to a plurality of elastic members in a curved pattern. The cleat attachment can be manufactured from one or more metals such as copper, aluminum, gold, silver, carbon (e.g., carbon nanotubes), or any other suitable metal. In some embodiments, the elongate members are wound/looped around (see FIG. 6B) the cleat attachment to prevent the elongate members from mechanical failure when stress is applied. In some embodiments, the cleat attachment can comprise a plurality of layers of heat adhesive TPU films such that desired levels of support, reinforcement and insulation are achieved. FIGS. 6B and 6C illustrate top and side view of the cleat attachment respectively in accordance with some embodiments.

Figure 7:
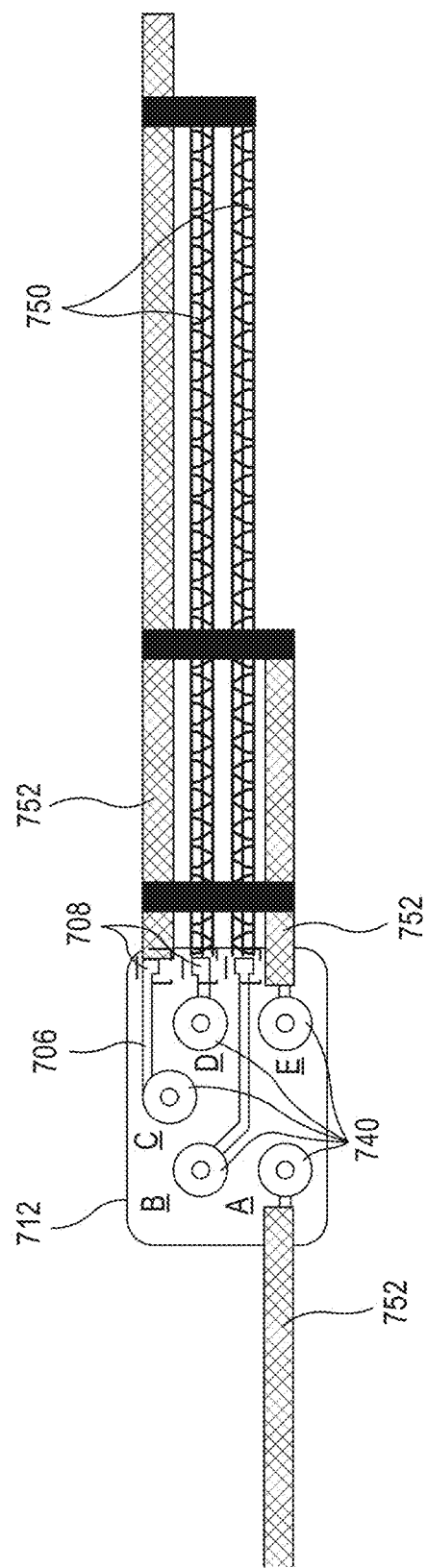
FIG. 7 is an illustration of conductive pathways, a plurality of connectors, a connection region with a PCB, and elongate members, in accordance with some embodiments.

FIG. 7 is an illustration of conductive pathways, plurality of connectors, connection region with PCB, and elongate members in accordance with some embodiments. In some embodiments, a plurality of connectors such as A, B, C, D, and E, collectively 740, traces 706, and contact pads 708 can be disposed on a PCB via SMT. The PCB with the connectors 740, the traces 706, and the contact pads 708 form a connection region 712. In such embodiments, conductive members such as conductive pathways/bands 752 are connected to the connectors 740 via hook attachments coupled to contact pads 708 in the connection region 712. The traces 706 and the contact pads 708 electrically connect the connectors 704 to the conductive pathways/bands 752. In FIG. 7, the connectors A, C, and E are connected to the conductive bands 752 that can be attached to textile based sensors (e.g., ECG sensors).

In a similar manner, connectors B and D are connected to conductive members such as elongate members 750 via cleat attachments coupled to the contact pads 708 (e.g., a RIP/breathing sensor) that extends or is looped around the garment. The elongate members 750 can be a stretchable tape that is knitted with a conductive wire or filament that is disposed in sinusoidal shape. In some embodiments, elongate members 750 can be wound/looped around the cleat attachment to prevent mechanical failure.

In some embodiments, the connectors 740 may include stainless steel snaps (e.g., comprising an S-spring socket and a hidden cap, or "snap cap") to couple the connection region 712 to an external device/component (e.g., electronics assembly 130 in FIG. 1). The caps can comprise stainless steel, brass, or any other suitable (i.e., biocompatible) material. In some embodiments, the connectors 740 may include a recess to couple an external device/component (e.g., electronics assembly 130 in FIG. 1) to the connection region 712. In such embodiments, the external device can include snaps comprising stainless steel, brass, or any other suitable (i.e., biocompatible material).

Figure 8:
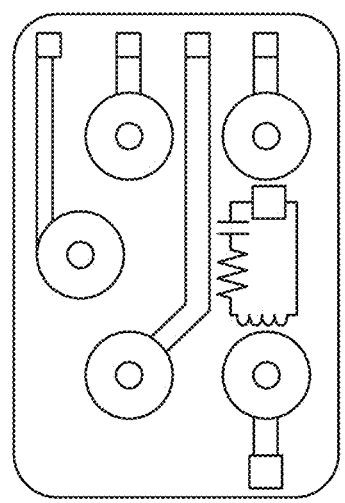
FIG. 8 illustrates a connection region including an electronics circuit, in accordance with some embodiments.

FIG. 8 illustrates a connection region including an electronics circuit in accordance with some embodiments. In some embodiments, the PCB can additionally include an electronics circuit 814 with electronic components such as analog to digital converters, microprocessors, measurement devices and/or the like. The electronic circuit can process signals from the sensor, communicate with user, convert analog signals to digital signals, transmit the signals to an external (i.e., remote) device, and receive signals from an external device and/or the like. In some embodiments, in addition to providing electronic connectivity, the electronic circuit 814 in the PCB can be configured to process data and enable communication with a user or an external device. In other words, components on the PCB can be configured to process and transmit (or receive) data to external device. The PCB can also include a rechargeable battery such that all of the signal processing from sensors embedded in the garment can be processed on the PCB without external hardware.

In this manner, connection region with a PCB interface offers several benefits. The PCB interface reduces form factor by enabling electronic connection between connectors and conductive members. The connection region can be manufactured by disposing the connectors in multiple configurations thereby providing design flexibility. Indirect coupling between the connectors and the conductive members via contact pads and attachments (e.g., hook and cleat) reduces the likelihood of contact failure.

Figure 9:
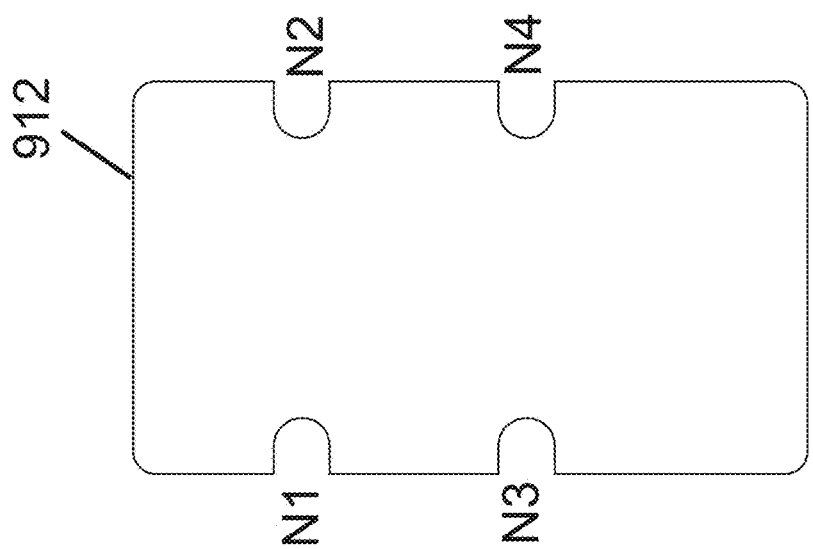
FIG. 9 illustrates a PCB substrate, in accordance with some embodiments.

In some embodiments, a PCB substrate is as shown in FIG. 9, having a substantially rectangular shape with rounded corners and a plurality of notches ("N1"-"N4") defined in edges of the PCB substrate 912. As shown in FIG. 9, two of the notches N1-N4 of the PCB substrate 912 are positioned on a first long edge of the PCB substrate 912, and two of the notches N1-N4 are positioned on a second long edge, opposite the first long edge, of the PCB substrate 912. The PCB substrate 912 has a thickness of about 0.6 mm, a width of about 14 mm, and a length (i.e., corresponding to the "long edge") of about 24 mm. Each of the notches N1-N4 Has a maximum depth, as measured inwardly from a perimeter of the PCB substrate 912, of about 2 mm. A first notch (N1, N2) on each long edge of the PCB substrate 912 can be positioned such that it extends from a distance about 5 mm from a first short edge of the PCB substrate 912, to a distance about 7 mm from the first short edge of the PCB substrate 912. Said another way, a center of the first notch can be positioned about 6 mm from the first short edge of the PCB substrate 912. A second notch (N3, N4) along each long edge of the PCB substrate 912 can be positioned such that it extends from a distance about 13 mm from a first short edge of the PCB substrate 912, to a distance about 15 mm from the first short edge of the PCB substrate 912. Said another way, a center of the second notch can be positioned about 14 mm from the first short edge of the PCB substrate 912. A distance from the center of the second notch to a second short edge of the PCB substrate 912 (the second short edge of the PCB substrate 912 disposed opposite the first short edge of the PCB substrate 912) is about 10 mm.

Figure 10:
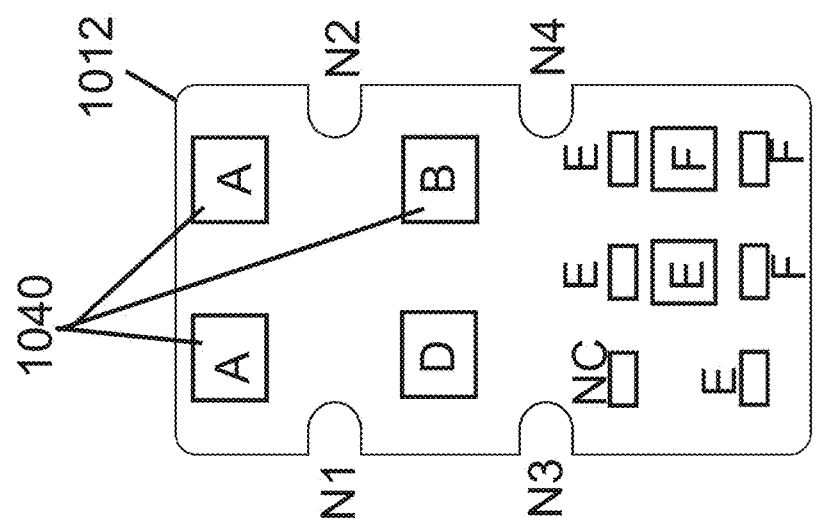
FIG. 10 illustrates a top layer of a PCB constructed using the PCB substrate of FIG. 9, in accordance with some embodiments.

FIG. 10 illustrates a top layer of a PCB 1012 constructed using the PCB substrate 912 of FIG. 9, in accordance with some embodiments. As shown in FIG. 10, a plurality of contact pads 1040 (labelled A, B, NC, D, E and F) of the top layer of the PCB 1012 are disposed on the PCB substrate. The contact pads 1040 can have a variety of shapes and sizes, and be arranged in a symmetric or asymmetric array. Exemplary contact pad dimensions include (as shown in FIG. 10), but are not limited to, about 2.6 mm× about 3 mm (see, e.g., contact pads A, D, B), about 1 mm× about 2 mm (see, e.g., contact pads NC, E, F), and about 2.4 mm× about 2.4 mm (see, e.g., contact pads E, F).

Figure 11:
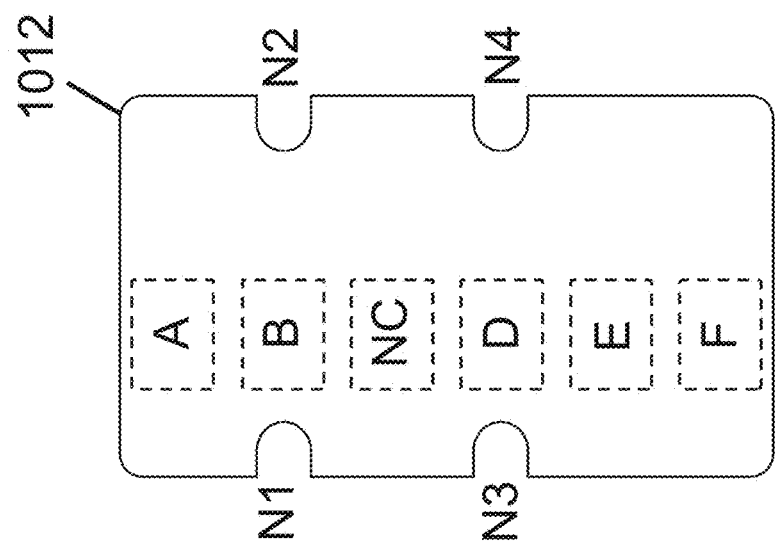
FIG. 11 illustrates a bottom layer of the PCB of FIG. 10.

FIG. 11 illustrates a bottom layer of the PCB of FIG. 10. The bottom layer of PCB 1012 includes a plurality of contact pads that are conductively coupled to corresponding contact pads (e.g., referenced by a common letter in FIG. 10) on the top layer of the PCB 1012. As shown in FIG. 11, contact pads A, B, NC, D, E and F are arranged in a single column configuration, and have a uniform shape of about 4 mm× about 3 mm. Adjacent contact pads are positioned about 4 mm apart, center-on-center. Although shown in FIG. 11 to have a column configuration, any geometric arrangement of the contact pads (e.g., symmetric or asymmetric array) is contemplated by the present disclosure, as determined by the design objectives or specifications of the particular implementation/application. Moreover, although particular dimensions and spacings of the contact pads are set forth herein for illustrative purposes, all other feasible dimensions and spacings are also contemplated, and such considerations can depend upon design rules and other application-specific constraints.

FIGS. 12A and 12B are further illustrations of the top and bottom layers, respectively, of the PCB of FIGS. 10 and 11. In accordance with some implementations, contact pads A, B and D of PCB 1012 are for electrical connection to an ECG sensor, contact pad NC is not subsequently connected to any other component (i.e., it is a "spare"), and contact pads E and F are for electrical connection to a breathing sensor.

Figure 13:
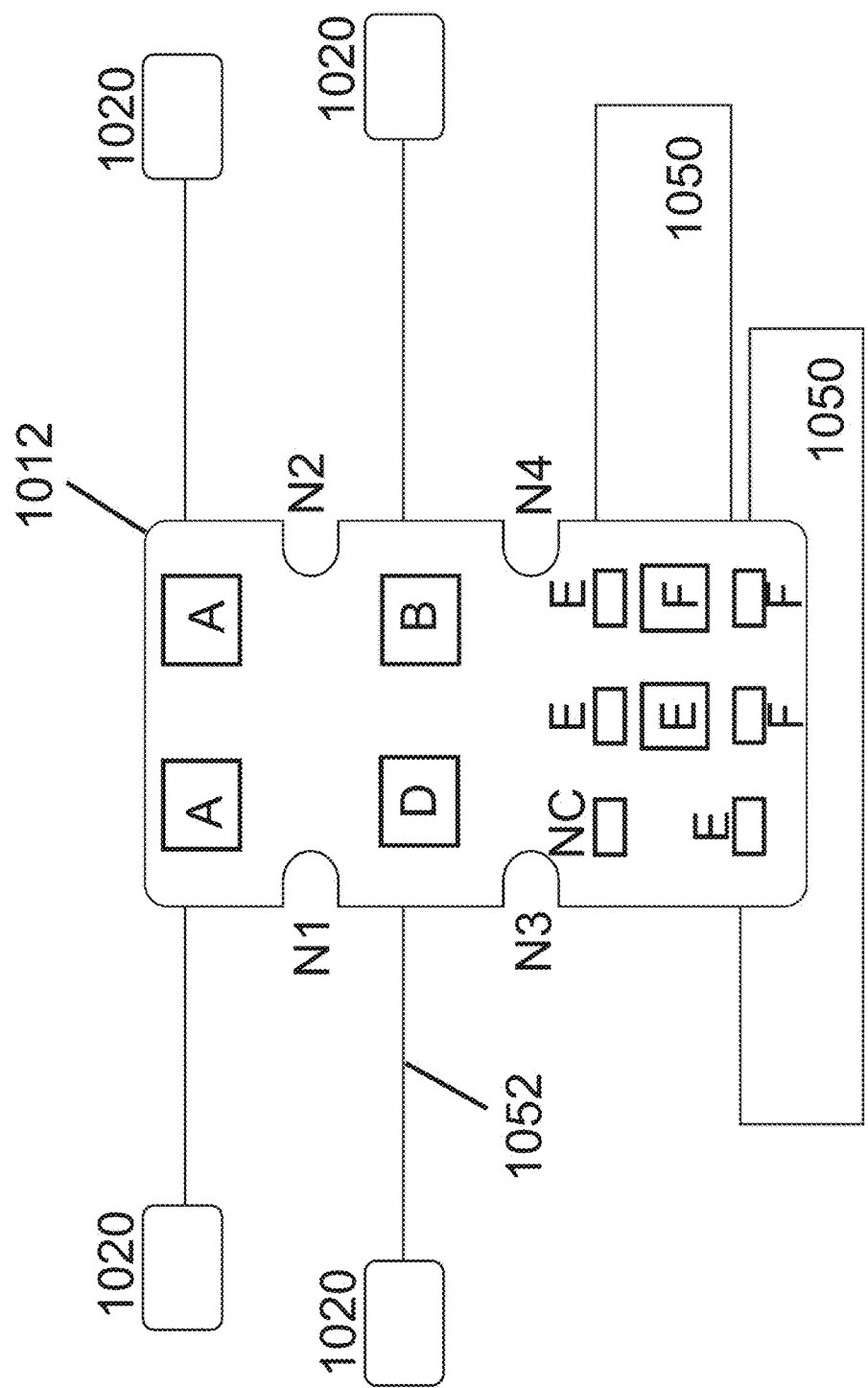
FIG. 13 illustrates a top layer of the PCB of FIGS. 10-11, with emanating conductive pathways and breathing sensors, in accordance with some embodiments.

FIG. 13 illustrates a top layer of the PCB of FIGS. 10-11, with emanating conductive pathways and breathing sensors, in accordance with some embodiments. The conductive pathways 1052 are conductively coupled to, and extend from, ECG contact pads A, B and D of PCB 1012. Each of the conductive pathways 1052 is also conductively and mechanically coupled to an associated electrode 1020. As used herein, the term "electrode" refers to an electrical conductor configured to contact a non-metallic surface including a skin of a user (e.g., a human or an animal) and to measure electrical signals corresponding to one or more physiological parameters of the user. Breathing sensors 1050 are conductively coupled to, and extend from, the breathing sensor contact pads E and F.

Figure 14:
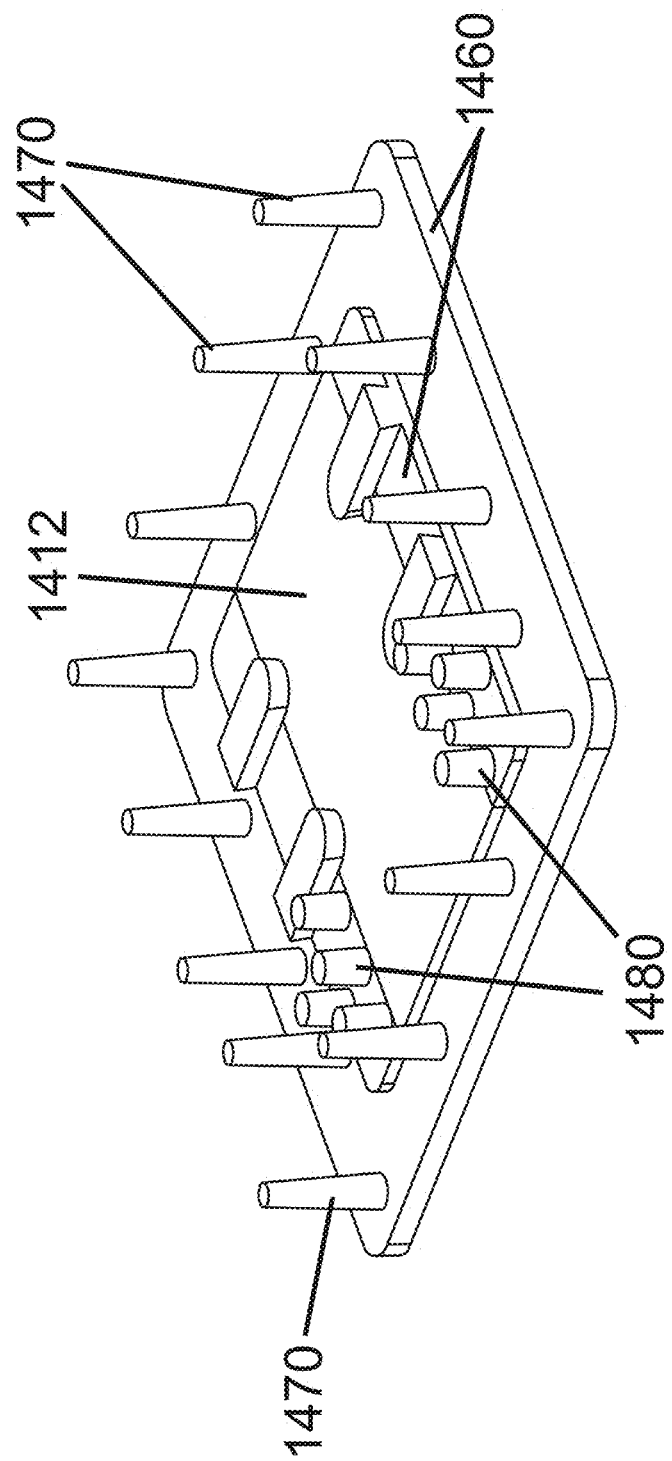
FIG. 14 illustrates a perspective top view of a PCB and box holder for connection to a base inner fabric/textile portion, in accordance with some embodiments.
Figure 15:
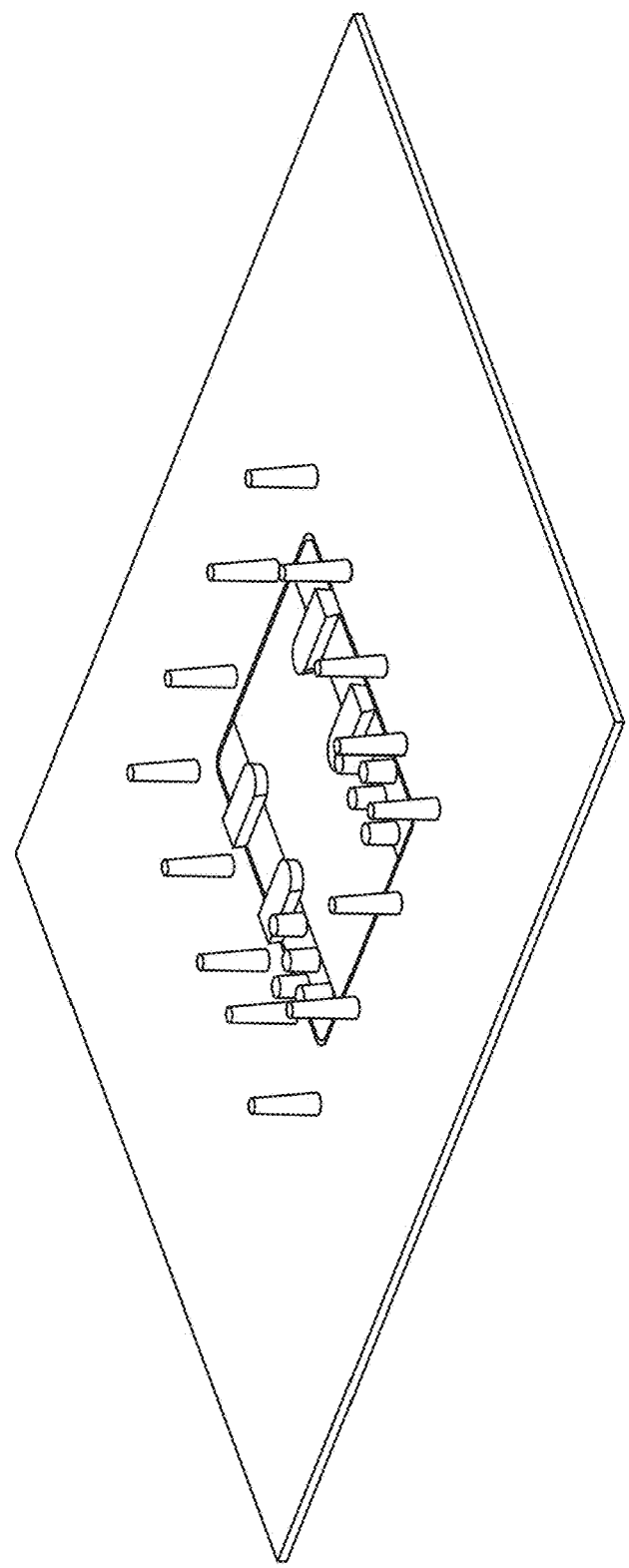
FIG. 15 illustrates the PCB and box holder of FIG. 14, coupled to the base inner fabric/textile portion.

FIG. 14 illustrates a perspective top view of a PCB 1412 that is received by and disposed within a box holder (also referred to herein as a "PCB holder," since it accommodates and mechanically restrains the PCB) 1460, for connection to a base inner (i.e., body-facing) fabric/textile portion, in accordance with some embodiments. When the box holder 1460 is connected to the fabric portion, the pins 1470 extend through the fabric, and can connect with a bottom plate that is configured to connect to the box holder 1460. Additional views of the box holder and bottom plate are shown and described with reference to FIGS. 18A-B and FIGS. 19A-C, below. Pins 1480 are configured to store (e.g., within a recess defined thereby) an excess/slack portion of one or more breathing sensor wires, so as to relieve tensile stress on the breathing sensor and/or to avoid breakage at the associated connection point. FIG. 15 illustrates the PCB and box holder of FIG. 14, when coupled to the base inner fabric/textile portion.

Figure 16B:
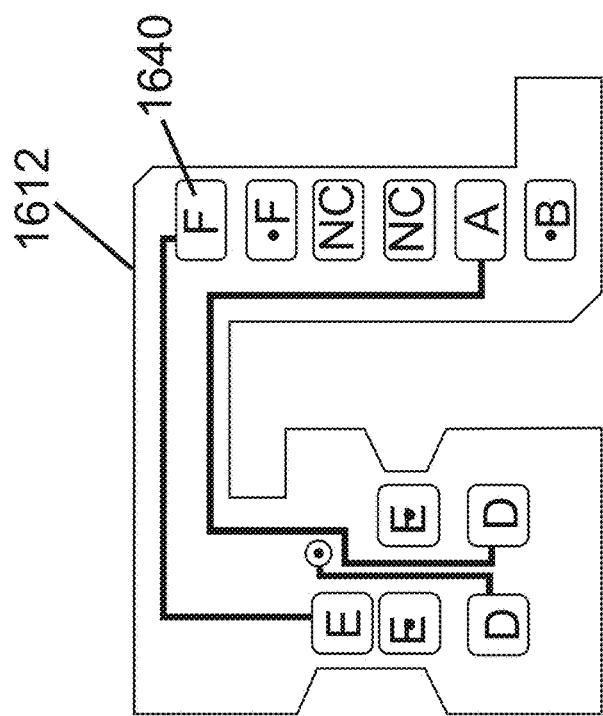
FIGS. 16A and 16B illustrate top and bottom layers, respectively, of a PCB in accordance with some embodiments.
Figure 16A:
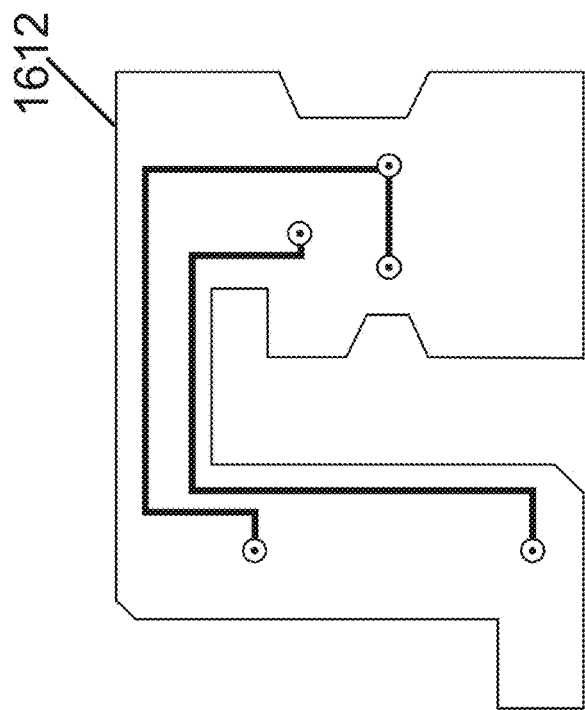

FIGS. 16A and 16B illustrate top and bottom layers, respectively, of a PCB 1612, including conductive plated through-holes for electrical connection, in accordance with some embodiments. The PCB 1612 includes a plurality of contact pads 1640, including contacts pads E and F for connection to one or more breathing sensors, contact pads A, B and D for connection to one or more ECG sensors, and spare contact pads NC.

Figure 17B:
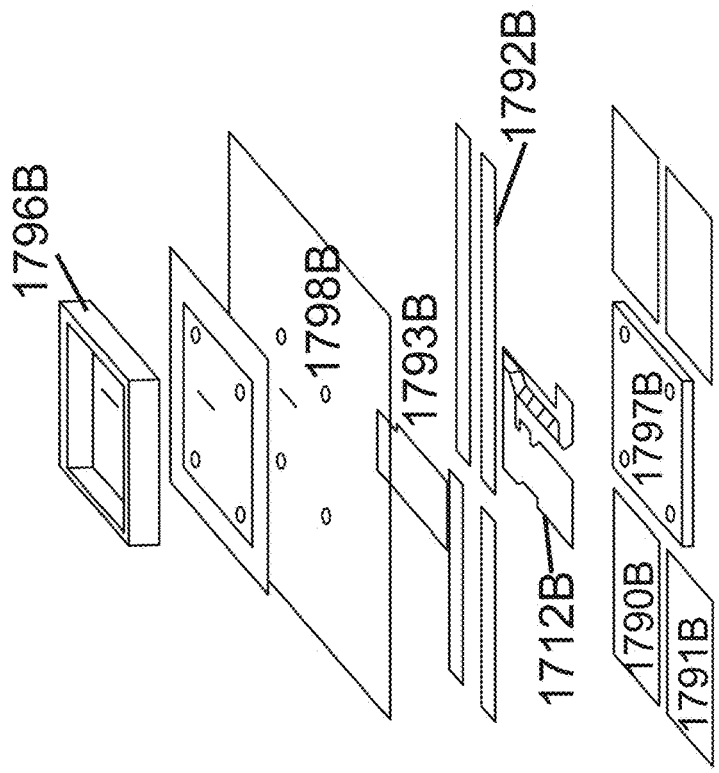
FIG. 17B illustrates a multilayer assembly process for a biosensing shirt, in accordance with some embodiments.
Figure 17A:
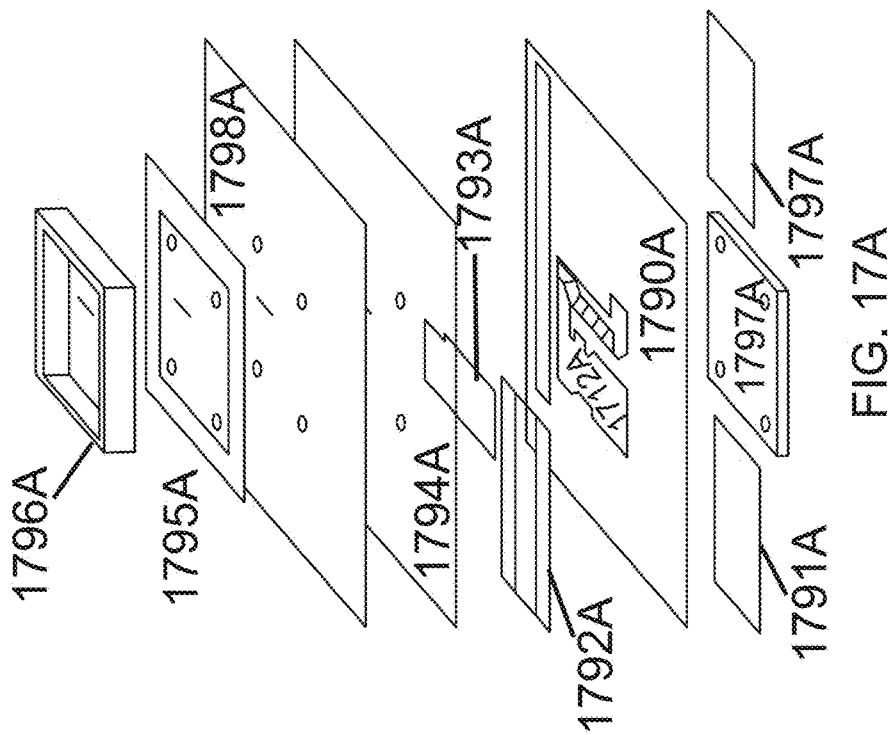
FIG. 17A illustrates a multilayer assembly process for a biosensing bra, in accordance with some embodiments.

FIG. 17A illustrates a multilayer assembly process for a biosensing bra, in accordance with some embodiments. As shown in FIG. 17A, a base 1797A is disposed at a bottom of the multilayer assembly, for supporting PCB 1712A, connection points of which extend through one or more corresponding openings in the inner layer of the textile/fabric 1790A. The base 1797A and fabric covers (for placement over electrodes of the biosensing bra) 1791A are disposed adjacent to a first surface of the inner layer of the textile/fabric 1790A. Disposed between a second surface (opposite the first surface) of the inner layer of the textile/fabric 1790A and a first surface of the elastic band 1794A are the breathing wire and ECG sensor traces 1792A and an isolation 1793A. A first surface of an outer layer textile/fabric portion 1798A is disposed adjacent to a second surface (opposite the first surface) of the elastic band 1794A. A transfer patch 1795A is disposed adjacent to (and affixed to) a second surface (opposite the first surface) of the outer layer textile/fabric portion 1798A and used to mechanically and electrically couple base 1796A to the outer layer textile/fabric portion 1798A. Through-holes for facilitating electrical connection between the layers of the multilayer assembly, the through-holes configured to substantially align with one another, are shown in the base 1797A, the elastic band 1794A, the outer layer textile/fabric portion 1798A, and the transfer patch 1795A.

FIG. 17B illustrates a multilayer assembly process for a biosensing shirt, in accordance with some embodiments. As shown in FIG. 17B, a base 1797B is disposed at a bottom of the multilayer assembly, for supporting PCB 1712B. The base 1797B, fabric covers (for placement over electrodes of the biosensing shirt) 1791B and textile covers (for placement over one or more breathing sensors) 1790B, are disposed adjacent to breathing wire and ECG traces 1792B. Disposed between the PCB connection region 1712B and a first surface of the out layer textile/fabric portion 1798B is an isolation 1793B. A transfer patch 1795B is disposed adjacent to (and affixed to) a second surface (opposite the first surface) of the outer layer textile/fabric portion 1798B and used to mechanically and electrically couple base 1796B to the outer layer textile/fabric portion 1798B. Through-holes for facilitating electrical connection between the layers of the multilayer assembly, the through-holes configured to substantially align with one another, are shown in the base 1797B, the outer layer textile/fabric portion 1798B, and the transfer patch 1795B.

Figure 18A:
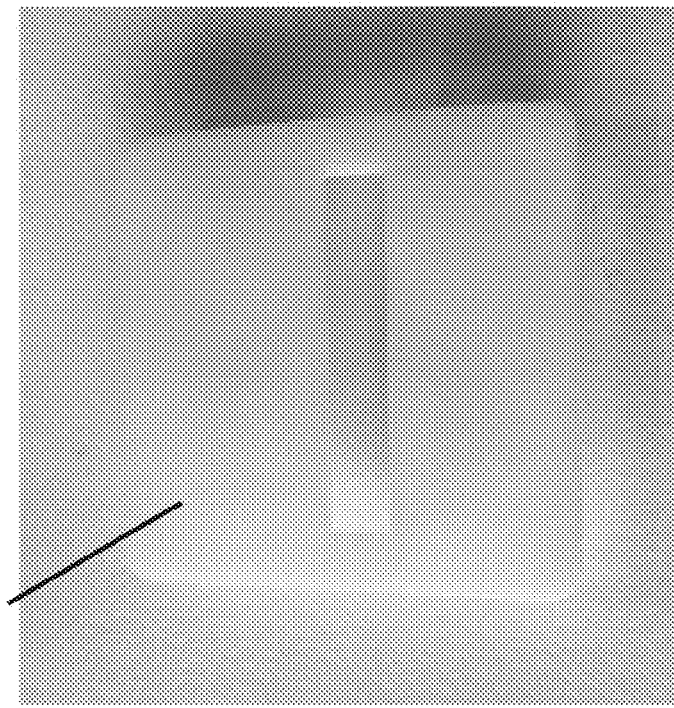
FIGS. 18A and 18B are photographic images of a first, body-facing side of a box holder, and a second side of the box holder that is opposite to the body-facing side, respectively, in accordance with a first embodiment.
Figure 18B:
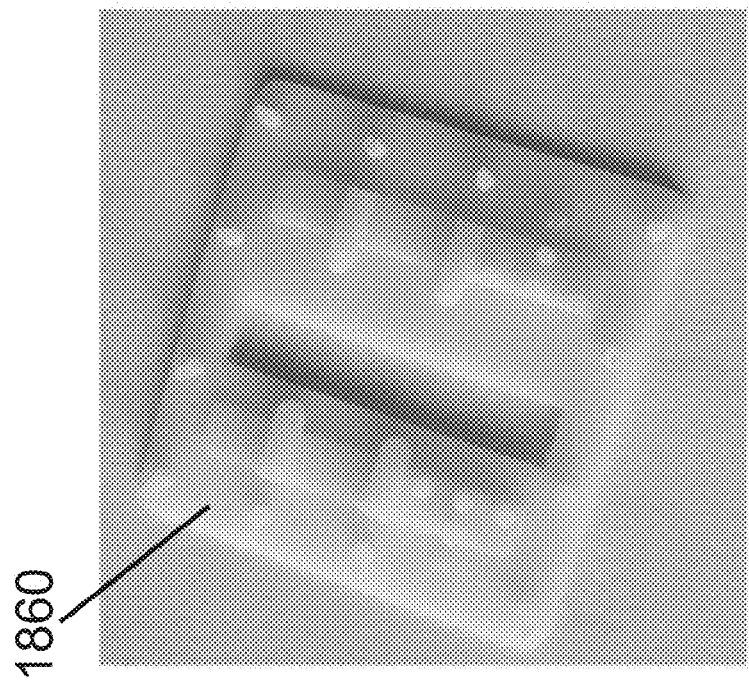

FIGS. 18A and 18B are photographic images of a first, body-facing side of a box holder 1860, and a second side of the box holder 1860 that is opposite to the body-facing side, respectively, in accordance with a first embodiment.

Figure 18D:
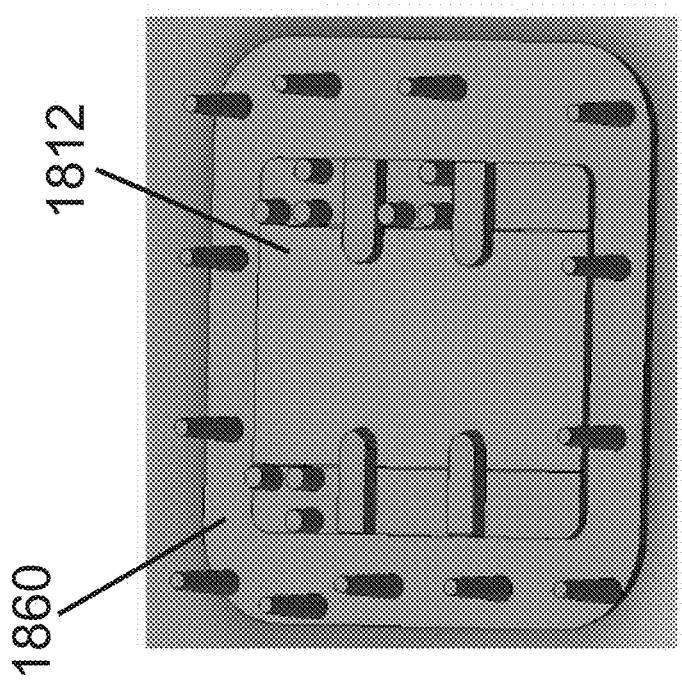
FIGS. 18C and 18D illustrate a first, body-facing side of a box holder without and with a PCB received therein, respectively, in accordance with a second embodiment.
Figure 18C:
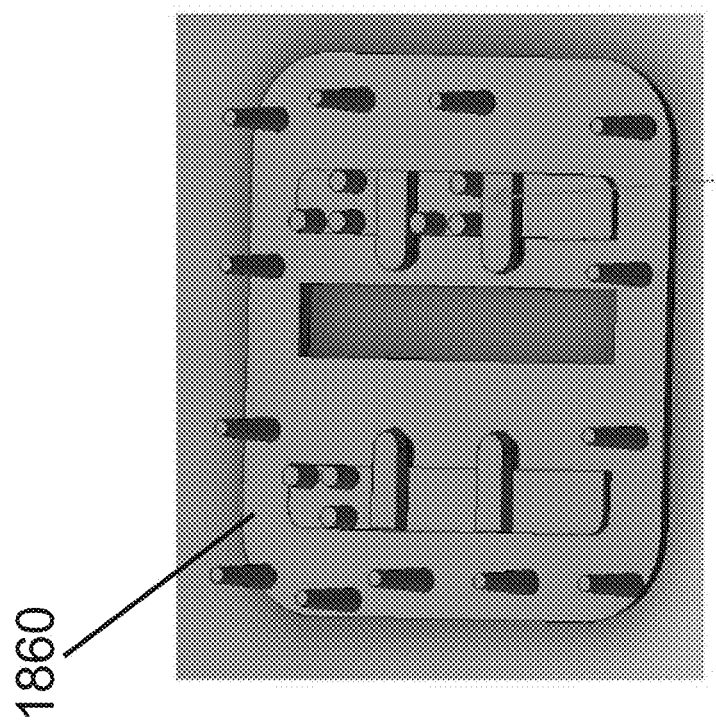

FIGS. 18C and 18D illustrate a first, body-facing side of a box holder 1860 without and with a PCB received therein, respectively, in accordance with a second embodiment. The box holder 1860 includes additional pins inward of the perimeter, which can be used for sensor attachment during an assembly process.

Figure 18E:
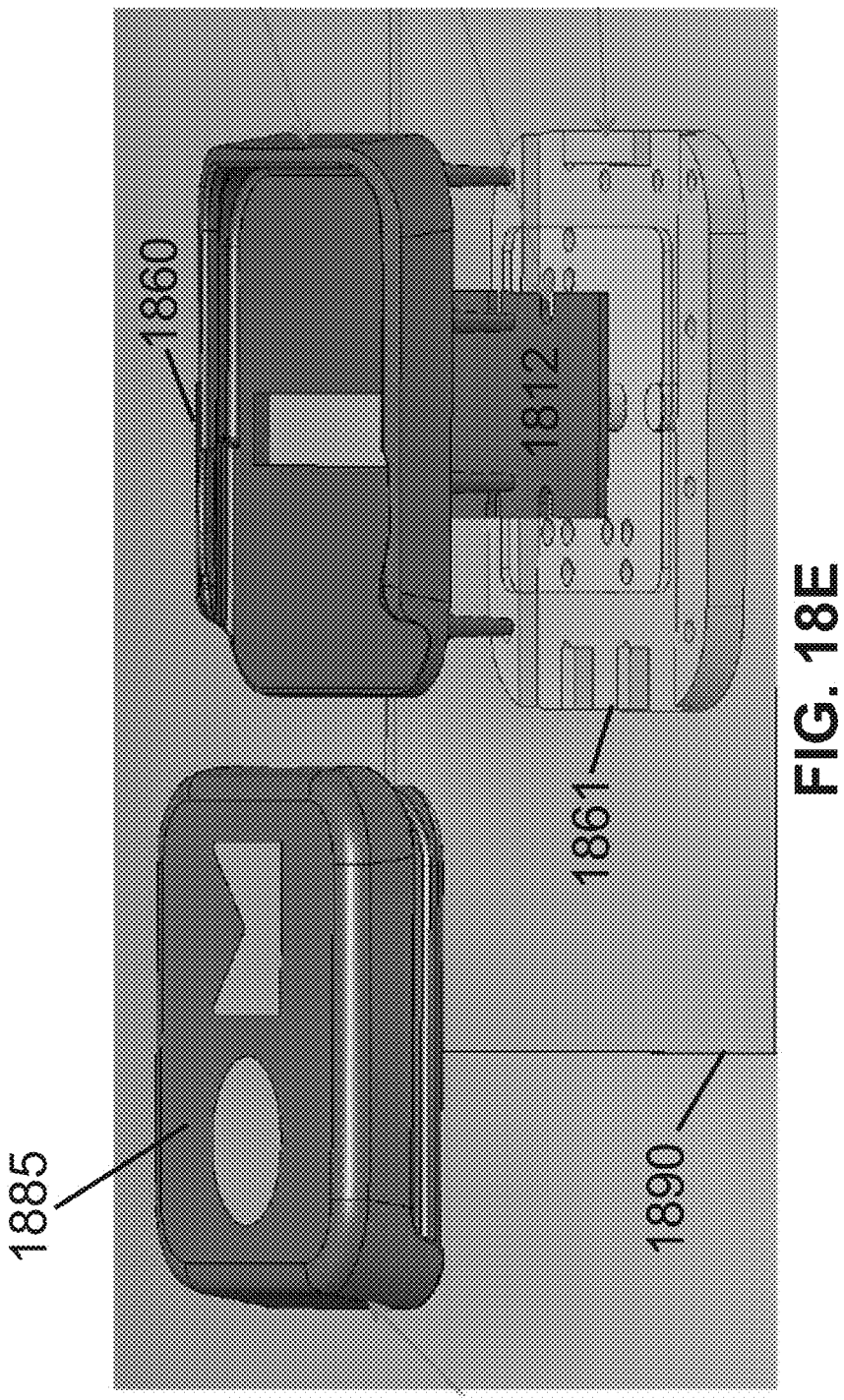

FIGS. 18E and 18F illustrate perspective, exploded views of a multilayer assembly for a biosensing garment, in accordance with some embodiments. As shown in FIGS. 18E and 18F, a bottom plate 1861 is disposed on a first side of a fabric/textile portion 1890 and aligned with a hole in the fabric/textile portion 1890. A PCB 1812 is disposed on and received by the bottom plate 1861, for example as shown in FIG. 18D. A first side of the box holder 1860 is disposed on a second side of the fabric/textile portion 1890 (the second side being opposite the first side) and is mechanically coupled (e.g., via complementary pins and recesses) to the bottom plate 1861 through the fabric/textile portion 1890. A second side of the box holder 1860, the second side being opposite of the first side, is configured to receive (e.g., slidably and/or removably receive) a hardware component 1885.

Figure 19A:
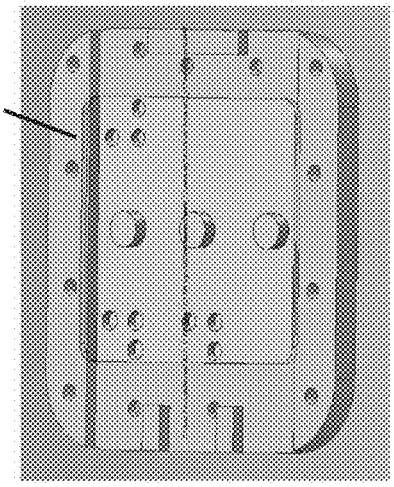
FIG. 19A is a photographic image of a first, body-facing side of a bottom plate, in accordance with some embodiments.
Figure 19B:
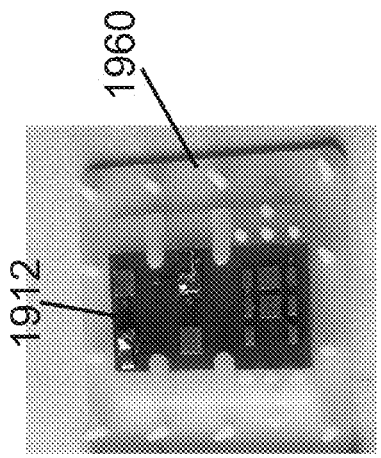
FIG. 19B illustrates a second side of a bottom plate that is opposite to a body-facing side thereof, in accordance with a first embodiment.
Figure 19D:
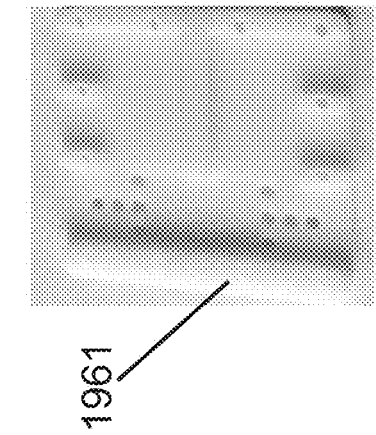
FIG. 19D is a photographic image of a box holder, containing a PCB received therein, configured to mechanically connect with the second side of the bottom plate of FIG. 19B of FIG. 19C.
Figure 19C:
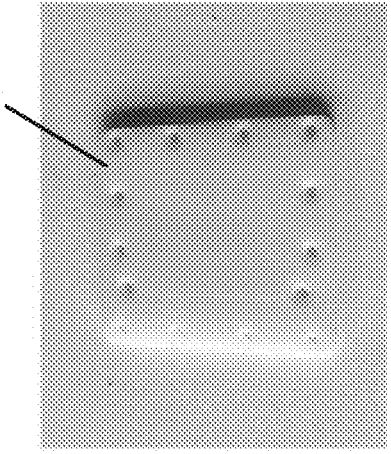
FIG. 19C is a photographic image of a second side of a bottom plate that is opposite to a body-facing side thereof, in accordance with a second embodiment.

FIG. 19A is a photographic image of a first, body-facing side of a bottom plate 1961, in accordance with some embodiments. FIG. 19B illustrates a second side of a bottom plate 1961 that is opposite to a body-facing side thereof, in accordance with a first embodiment. FIG. 19C is a photographic image of a second side of a bottom plate that is opposite to a body-facing side thereof, in accordance with a second embodiment. FIG. 19D is a photographic image of a box holder 1960, containing a PCB 1912 received therein, the box holder 1960 configured to mechanically connect (e.g., via complementary pins and recesses) with the second side of the bottom plate 1961 of FIG. 19B or the bottom plate 1961 of FIG. 19C.

Figure 20B:
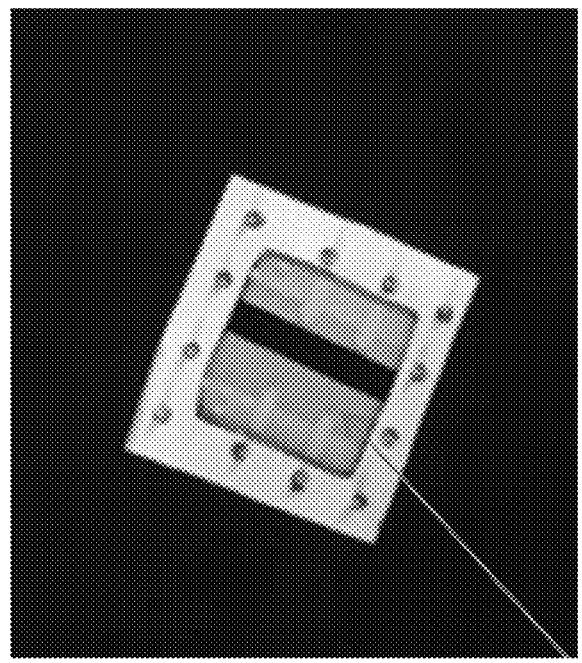
FIGS. 20A-20E are photographic images showing an assembly process, in accordance with some embodiments.
Figure 20A:
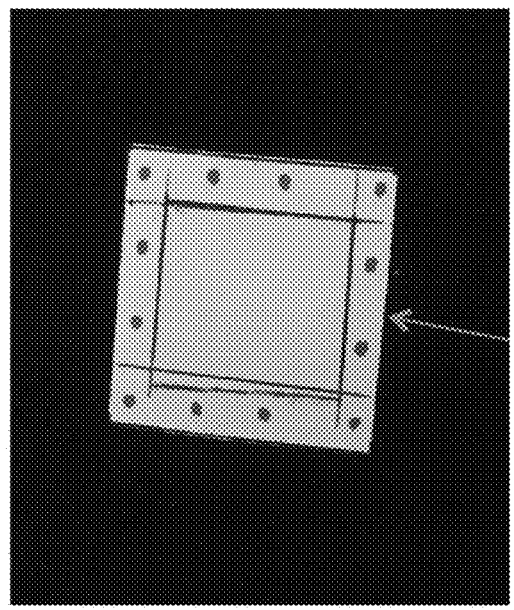
Figure 20D:
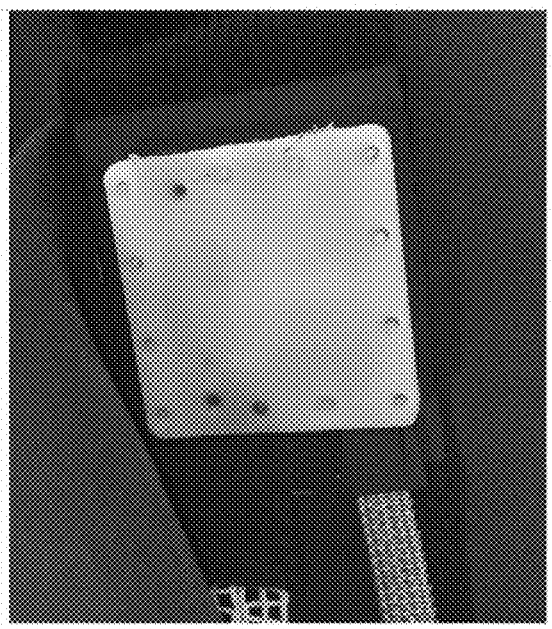
Figure 20C:
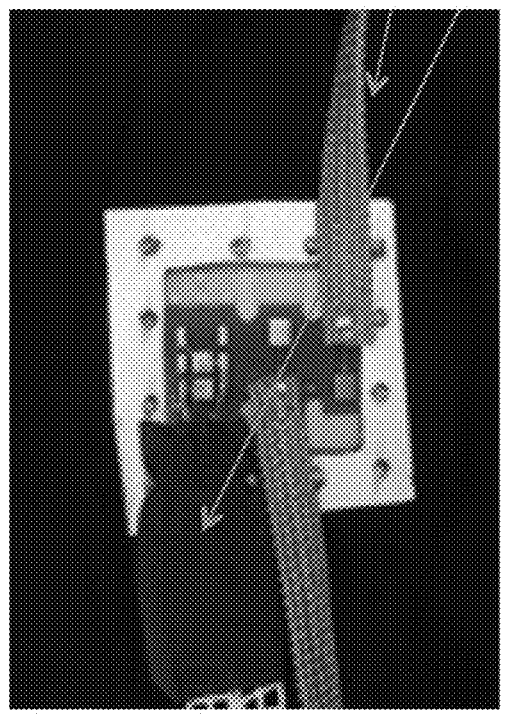
Figure 20E:
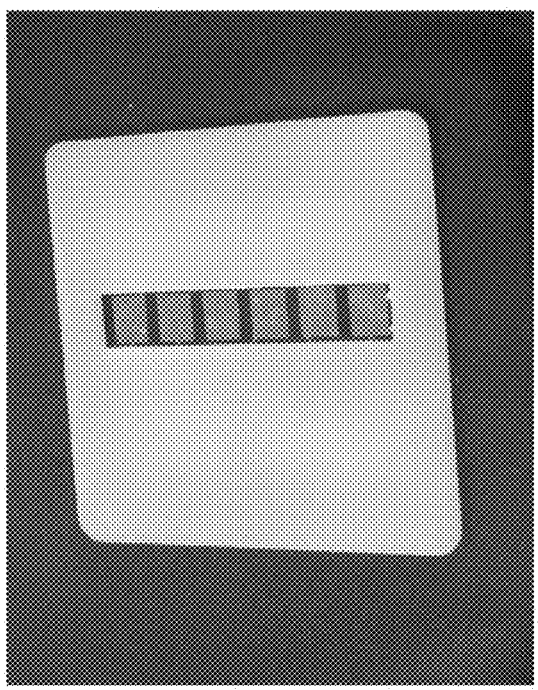

FIGS. 20A-20E are photographic images showing an assembly process for a box holder, in accordance with some embodiments. In a first step, shown in FIG. 20A a hole is created in a textile/garment, the hole sized to accommodate the PCB and box holder. FIG. 20B is an exterior/outer view (i.e., a side configured to face away from the body of a wearer during use) showing the PCB and box holder when placed within the hole. FIG. 20C shows an interior (body-facing) view of the PCB and box holder of FIG. 20B, with a sensor (e.g., a breathing sensor) and conductive pathways connected to the PCB. In some embodiments, a layer of insulation (e.g., including a polymer) is applied to the assembly to cover and electrically insulate the conductive pathways and/or sensors (or portions thereof). FIG. 20D shows the body-facing view of the box holder assembly as shown in FIG. 20C, but with a bottom plate coupled thereto. In other words, the second side of the bottom plate (shown in FIG. 19B) is positioned over and aligned with the box holder of FIG. 20C, and mechanically coupled thereto (e.g., via press-fit, adhesive, etc.). FIG. 20E shows the exterior view (i.e., as viewed opposite the body-facing side) of the box holder assembly shown in FIG. 20D. The outer surface of the box holder assembly is configured to mechanically and/or electrically receive additional hardware (i.e., an electronics "box"), for example via slidable attachment using one or more tracks disposed on the box assembly.

As used herein, the terms "about" and "approximately" generally mean plus or minus 10% of the value stated, for example about 250 µm would include 225 µm to 275 µm, about 1,000 µm would include 900 µm to 1,100 µm.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A biosensing garment connector, comprising:
   a printed circuit board (PCB) including a plurality of flexible, non-stretchable layers;
   a plurality of connectors disposed on the PCB, each connector of the plurality of connectors electrically coupled to a trace of a plurality of traces of the PCB;
   a plurality of contact pads disposed on the PCB, each contact pad of the plurality of contact pads electrically coupled to an associated connector of the plurality of connectors via the associated trace of the plurality of traces; and
   a plurality of attachments, each attachment of the plurality of attachments mechanically and electrically coupled to an associated contact pad of the plurality of contact pads;
   the PCB configured to electrically couple the plurality of connectors to a portion of a garment including at least one conductive member.

2. The biosensing garment connector of claim 1, wherein at least one of the plurality of attachments comprises one of a cleat or a hook.

3. The biosensing garment connector of claim 1, wherein the plurality of connectors comprise at least one of: copper, aluminum, gold, silver, or carbon.

4. The biosensing garment connector of claim 1, wherein the PCB further includes an isolation coating disposed on at least a portion of the plurality of traces to prevent corrosion.

5. The biosensing garment connector of claim 1, wherein the PCB further includes a rechargeable battery, and is further configured to perform, without external hardware, signal processing on signals received from at least one sensor of the garment.

6. The biosensing garment connector of claim 1, wherein the plurality of connectors, the plurality of traces, the plurality of contact pads, and the plurality of attachments, are supported on a first side of the PCB.

7. An apparatus, comprising:
   a garment, including at least one sensor and at least one conductive member, each conductive member of the at least one conductive member electrically coupled to a sensor of the at least one sensor;
   a printed circuit board (PCB) including a plurality of flexible, non-stretchable layers, mechanically coupled to the garment and electrically coupled to the at least one sensor and to the at least one conductive member;
   a plurality of connectors disposed on the PCB for connection to an electronics assembly, each connector of the plurality of connectors electrically coupled to a trace of a plurality of traces of the PCB;
   a plurality of contact pads disposed on the PCB, each contact pad of the plurality of contact pads electrically coupled to an associated connector of the plurality of connectors via the associated trace of the plurality of traces; and
   a plurality of attachments, each attachment of the plurality of attachments mechanically and electrically coupled to an associated contact pad of the plurality of contact pads.

8. The apparatus of claim 7, wherein the PCB is mechanically coupled to the garment along at least one edge of the PCB via a composite material.

9. The apparatus of claim 8, wherein the composite material comprises at least one of rubber or silicone.

10. The apparatus of claim 7, wherein the PCB is electrically coupled to the at least one sensor and and the at least one conductive member via at least one attachment of the plurality of attachments, and the attachment comprises one of a hook or a cleat.

11. The apparatus of claim 7, wherein the PCB further includes a rechargeable battery, and is further configured to perform, without external hardware, signal processing on signals received from sensors of the garment.

12. The apparatus of claim 7, wherein the plurality of connectors, the plurality of traces, the plurality of contact pads, and the plurality of attachments, are supported on a first side of the PCB.

13. A system, comprising:
   a biosensing garment, including at least one sensor and at least one conductive member, each conductive member of the at least one conductive member electrically coupled to a sensor of the at least one sensor;
   a printed circuit board (PCB) including a plurality of flexible, non-stretchable layers, mechanically coupled to the biosensing garment and electrically coupled to the at least one sensor and to the at least one conductive member;
   a plurality of connectors disposed on the PCB for connection to an electronics assembly, each connector of the plurality of connectors electrically coupled to a trace of a plurality of traces of the PCB;
   a plurality of contact pads disposed on the PCB, each contact pad of the plurality of contact pads electrically coupled to an associated connector of the plurality of connectors via the associated trace of the plurality of traces;

a plurality of attachments, each attachment of the plurality of attachments mechanically and electrically coupled to an associated contact pad of the plurality of contact pads; and a flexible electronics assembly, including a battery, an antenna, a transceiver, a sensor, and a microprocessor, the electronics assembly electrically and mechanically coupled to the PCB, the microprocessor configured to transduce and analyze an analog signal received from the sensor.

14. The system of claim 13, wherein the microprocessor is further configured to convert the analog signal to a digital signal and send the digital signal to a remote device.

15. The system of claim 13, wherein the PCB is mechanically coupled to the biosensing garment along at least one edge of the PCB via a composite material.

16. The system of claim 15, wherein the composite material comprises at least one of rubber or silicone.

17. The system of claim 13, wherein the PCB is electrically coupled to the at least one conductive member via a hook-type attachment.

18. The system of claim 13, wherein the PCB is electrically coupled to the at least one conductive member via a cleat-type attachment.

19. The system of claim 13, wherein the biosensing garment comprises one of: a shirt, shorts, pants, a brassiere, a headband, an arm band, a leg band, or a wrist band.

20. The system of claim 13, wherein the plurality of connectors, the plurality of traces, the plurality of contact pads, and the plurality of attachments, are supported on a first side of the PCB.

\* \* \* \* \*